US011638685B2

(12) United States Patent
Fei et al.

(10) Patent No.: US 11,638,685 B2
(45) Date of Patent: May 2, 2023

(54) HAIR CARE COMPOSITION (71) Applicant: Conopco, Inc., Englewood Cliffs, NJ (US)

(72) Inventors: Congwei Fei, Shanghai (CN); Yingying Pi, Shanghai (CN); Raghupathi Subramanian, Shanghai (CN)

(73) Assignee: CONOPCO, INC., Englewood Cliffs, NJ (US)

( * ) Notice: Subject to any disclaimer, the term of this patent is extended or adjusted under 35 U.S.C. 154(b) by 181 days.

(21) Appl. No.: 16/767,679

(22) PCT Filed: Nov. 14, 2018

(86) PCT No.: PCT/EP2018/081223
§ 371 (c)(1),
(2) Date: May 28, 2020

(87) PCT Pub. No.: WO2019/110253
PCT Pub. Date: Jun. 13, 2019

(65) Prior Publication Data
US 2020/0289397 A1 Sep. 17, 2020

(30) Foreign Application Priority Data

Dec. 8, 2017 (WO) ................ PCT/CN2017/115307
Jan. 17, 2018 (EP) .................................... 18152005

(51) Int. Cl.
| | |
|---|---|
| *A61Q 5/02* | (2006.01) |
| *A61Q 5/12* | (2006.01) |
| *A61K 8/81* | (2006.01) |
| *A61K 8/46* | (2006.01) |
| *A61Q 5/00* | (2006.01) |

(52) U.S. Cl.
CPC .............. *A61K 8/817* (2013.01); *A61K 8/463* (2013.01); *A61K 8/8158* (2013.01); *A61Q 5/006* (2013.01); *A61Q 5/02* (2013.01); *A61Q 5/12* (2013.01); *A61K 2800/5426* (2013.01); *A61K 2800/58* (2013.01); *A61K 2800/59* (2013.01)

(58) Field of Classification Search
None
See application file for complete search history.

(56) References Cited

U.S. PATENT DOCUMENTS

| | | | | |
|---|---|---|---|---|
| 5,037,818 | A * | 8/1991 | Sime ........................ | A61Q 5/02 424/70.13 |
| 8,003,088 | B2 | 8/2011 | Yoda et al. | |
| 2003/0108507 | A1 | 6/2003 | Clipson et al. | |
| 2011/0294773 | A1 * | 12/2011 | Ishikubo ................ | A61K 8/817 514/188 |

(Continued)

FOREIGN PATENT DOCUMENTS

| | | |
|---|---|---|
| CN | 1568174 | 1/2005 |
| CN | 105307726 | 2/2016 |

(Continued)

OTHER PUBLICATIONS

Search Report and Written Opinion in EP18152005; dated Jun. 14, 2018.
Search Report and Written Opinion in PCTEP2018081223; dated Jan. 3, 2019.
IRPR2 in PCTEP2018081223; dated Oct. 25, 2019.
Liu, Yun; Detergent Principle Material Process Formulation; Chemical Industry Press; Sep. 30, 1998; p. 75, with translation; China, p. 75, paragraph 4 only.

(Continued)

*Primary Examiner* — Jyothsna A Venkat
(74) *Attorney, Agent, or Firm* — Foley & Lardner LLP (57) ABSTRACT

A hair care composition is disclosed comprising a copolymer, an ethoxylated alkyl sulfate anionic surfactant having a formula $RO(CH_2CH_2O)nSO_3M$, wherein R is an alkyl or alkenyl having from 8 to 18 carbon atoms; M is a solubilising cation comprising sodium, potassium, ammonium or mixtures thereof; the degree of ethoxylation n is 2, and from 0.01 to 5% by weight of a zinc-based anti-dandruff agent; wherein the copolymer comprises: a cationic vinyl monomer A represented by the formula: $CH_2=C(R^1)-CO-NH-(CH_2)_dN^+R^2R^3R^4X^-$, wherein $R^1$ is a hydrogen atom or a methyl group, each of $R^2$ to $R^4$ is independently a $C_{1-24}$ alkyl group, preferably a $C_{1-3}$ alkyl group, $X^-$ is independently fluoride, chloride, bromide or iodide anion, preferably chloride, and d is an integer of from 1 to 10; a cationic vinyl monomer B represented by the formula: $CH_2=C(R^5)-CO(O)-(CH_2)_eN^+R^6R^7R^8Y^-$, wherein $R^5$ is a hydrogen atom or a methyl group, each of $R^6$ to $R^8$ is independently a $C_{1-24}$ alkyl group, preferably a $C_{1-3}$ alkyl group, $Y^-$ is independently fluoride, chloride, bromide or iodide anion, preferably chloride, and e is an integer of from 1 to 10; a vinyl monomer C represented by the formula: $CH_2=C(R^9)-CO-NR^{10}R^{11}$, wherein $R^9$ is a hydrogen atom or methyl group, each of $R^{10}$ and $R^{11}$ is independently a hydrogen atom or a $C_{1-4}$ alkyl group, provided that the sum of carbon numbers of $R^{10}$ and $R^{11}$ is from 1 to 4; and wherein the content of monomer A is from 1 to 44 mol % based on the total monomer content of the copolymer, the content of monomer B is from 1 to 44 mol %, and the content of monomer C is from 20 to 75 mol % based on the total monomer content of the copolymer.

4 Claims, 2 Drawing Sheets

(56) References Cited

U.S. PATENT DOCUMENTS

2013/0150338 A1    6/2013  Ananthapadmanabhan et al.
2015/0011450 A1    1/2015  Carter et al.
2016/0317424 A1  11/2016  Kadir et al.

FOREIGN PATENT DOCUMENTS

| EP | 0093601 | 10/1987 |
|----|---------|---------|
| JP | S58196300 | 11/1983 |
| JP | 2006516022 | 6/2006 |
| JP | 2017501225 | 1/2017 |
| KR | 20080099393 | 11/2008 |
| KR | 20090120955 | 11/2009 |
| WO | WO9631188 | 10/1996 |
| WO | WO03094874 | 11/2003 |
| WO | WO2004035015 | 4/2004 |
| WO | WO2013011122 | 1/2013 |
| WO | WO2014095625 | 6/2014 |
| WO | WO2016058836 | 4/2016 |
| WO | WO2016058837 | 4/2016 |
| WO | WO2016100466 | 6/2016 |

* cited by examiner

HAIR CARE COMPOSITION

CROSS REFERENCE TO RELATED APPLICATION

This application is a U.S. National Stage Application under 35 U.S.C. § 371 of International Application No. PCT/EP2018/081223, filed on Nov. 14, 2018, which claims the benefit of European Application No. 18152005.7, filed on Jan. 17, 2018 and International Application No. PCT/CN2017/115307, filed on Dec. 8, 2017, the entire disclosures of which are hereby incorporated by reference for any and all purposes.

TECHNICAL FIELD OF THE INVENTION

This invention relates to a hair care composition, especially a hair care composition comprising a copolymer, a specific anionic surfactant and a zinc-based anti-dandruff agent that results in smaller flocculation size and enhanced anti-dandruff agents delivery efficiency to hair and/or scalp to ensure maximum anti-microbial efficacy.

BACKGROUND OF THE INVENTION

Hair care compositions generally provide cleansing or conditioning benefits or a combination of the two. Such compositions typically comprise one or more cleansing surfactants which generally aid in cleaning the hair and the scalp free of undesirable soil, particles and fatty matter. Conditioning benefit is achieved by including one or more conditioning agents in the hair care composition. Conditioning benefit is delivered with an oily material being deposited onto the hair resulting in the formation of a film, which makes the hair easier to comb when wet and more manageable when dry.

Additionally, anti-dandruff benefit has been provided through hair care compositions. Dandruff is an issue that affects many people globally. The condition is manifested by the shedding of clumps of dead skin cells from the scalp. These are white in colour and provide an aesthetically displeasing appearance. A factor that contributes to dandruff is certain members of the Malassezia yeasts. To combat these, anti-dandruff products have included certain anti-dandruff agents which have anti-fungal activity. Such a product has to perform as a hair cleansing shampoo, while mitigating the causes of dandruff. Therefore, it is always desired to improve the delivery efficiency of anti-dandruff agents to maximize the effectiveness of such anti-dandruff agents.

Typical anti-dandruff agents used in hair care are metal pyrithione salts e.g zinc pyrithione, piroctone olamine (octopirox), azole based anti-fungal agents (e.g. climbazole), selenium sulfide and combinations thereof. Of these, zinc pyrithione is a particulate material.

Cationic polymers are often used to enhance the deposition of the conditioning agent and/or anti-dandruff agents onto hair and/or scalp. These polymers may be synthetic or natural polymers that have been modified with cationic substituents.

However, it is well accepted that cationic polymers and anionic surfactants form polymer-surfactant complex (flocculation) within a shampoo system to help deposit anti-dandruff agents. The flocculation profile affects the delivery efficiency of anti-dandruff agents to scalp and its distribution on the scalp. It is proven in clinical experiments that big flocculation size is not desirable for anti-dandruff efficacy since anti-dandruff agents may be trapped in the big flocculation particles and hard to be released. It has been found that the degree of substitution (DS) and molecular weight (MW) of cationic polymers play a critical role in the flocculation profile of anti-dandruff shampoo. For example, higher DS drives better deposition of anti-dandruff agents but leads to faster flocculation speed which results in bigger flocculation particles formation.

The present inventors have now recognized a need to develop a hair care composition that can deliver satisfactory flocculation profile while maintaining good deposition of anti-dandruff agents. It has been found unexpectedly that this need can be met by using a combination of a copolymer and an ethoxylated anionic surfactant with a specific degree of ethoxylation in a hair care composition.

Additional Information

WO 2016/100466 A1 discloses a hair care composition comprising: i) at least one crosslinked nonionic amphiphilic suspending polymer; ii) at least one anionic surfactant; iii) at least one particulate anti-dandruff agent; and iv) water. The suspending polymer is a pH independent nonionic, amphiphilic emulsion polymer that is crosslinked with an amphiphilic crosslinking agent and effectively suspends water insoluble particulate anti-dandruff agents.

The additional information above does not describe a hair care composition comprising a copolymer comprising constituting units of specific cationic vinyl monomers and constituting units of a specific vinyl monomer in a specific ratio, an ethoxylated anionic surfactant with a specific degree of ethoxylation, and a zinc-based anti-dandruff agent; and especially such a hair care composition can deliver satisfactory flocculation profile while maintaining good deposition of anti-dandruff agents.

Tests and Definitions

Hair Care Composition

"Hair care composition", as used herein, is meant to include a composition for topical application to hair and/or scalp of mammals, especially humans. Such a composition may be generally classified as leave-on or rinse off, and includes any product applied to a human body for also improving appearance, cleansing, odor control or general aesthetics. The composition of the present invention can be in the form of a liquid, lotion, cream, foam, scrub, gel, or bar. Non-limiting examples of such compositions include leave-on hair lotions, creams, and rinse-off shampoos, conditioners, shower gels, or toilet bar. The composition of the present invention is preferably a rinse-off composition, especially preferred being a shampoo or a conditioner and most preferably a shampoo.

Delivery Efficiency

"Delivery efficiency", as used herein, refers to the ability to deliver and deposit anti-dandruff agents on scalp surfaces of an individual.

Cationic Charge Density

"Cationic charge density", as used herein, refers to the number of cationic charges per weight unit of a given polymer. Cationic charge density can be calculated from the degree of substitution as described in WO 2013/011122, the disclosure of which is hereby incorporated by reference in its entirety but especially page 8 lines 8-17. For example, for cationically-modified guar polymer obtained by reacting with 2,3-epoxypropyltrimethylammonium chloride, the cationic charge density may be calculated from the DS using the following equation:

$$\text{Cationic charge density in milliequivalents per gram (meq/g)} = \frac{DS \times 1000}{162 + 151 \times DS}$$

Degree of Ethoxylation

"Degree of Ethoxylation", as used herein, refers to the average number of moles of ethylene oxide unit per mole of ethoxylated product. The degree of ethoxylation is measured using $^1$H NMR in a solvent of deuterium oxide (D$_2$O). For example, the degree of ethoxylation of sodium laureth sulfate (SLES) is measured using $^1$H NMR (Bruker-Biospin, 400 MHz) and the spectrum is recorded at 25° C. The sample for measurement using NMR is prepared as follows: the sample is dispersed in D$_2$O in a centrifugal tube and sonicated, then the solution is filtered and transferred to an NMR tube. The peaks corresponding to the protons of the sample appear at about 3.98 ppm, about 4.15 ppm and between about 3.58 to about 3.84 ppm. The peaks corresponding to the protons for —CH$_2$—, which appear at about 4.15 ppm and about 3.98 ppm, are integrated as A1. The peaks corresponding to the four protons for —OCH$_2$CH$_2$—, which appear at 4.15 ppm and between about 3.58 to about 3.84 ppm, are also integrated as A2. The degree of ethoxylation of SLES may be calculated as follows:

$$\text{The degree of ethoxylation} = \frac{(A2/4)}{(A1/2)}$$

Average Particle Size

"Average particle size", as used herein, refers to the volume average particle size as measured using light scattering technique with a Malvern Mastersizer 2000 instrument. The settings used for the measurement included a particle absorption of 0.1, with water as the dispersant an obscuration limit of 10-12% and a pump-speed of 960 rpm. The average particle size of a sample was measured from the particle size distribution curves as an average of three sample readings.

Water-Insoluble

"Water-insoluble", as used herein, refers to the solubility of a material in water at 25° C. and atmospheric pressure being 0.1% by weight or less.

Molecular Weight

"Molecular weight", as used herein, refers to the weight average molecular mass of a given polymer. The weight average molecular weight of copolymer may be measured by gel permeation chromatography (using e.g. water/methanol/acetic acid/sodium acetate as a developing solvent).

Miscellaneous

Except in the examples, or where otherwise explicitly indicated, all numbers in this description indicating amounts of material or conditions of reaction, physical properties of materials and/or use may optionally be understood as modified by the word "about".

All amounts are by weight of the final oral care composition, unless otherwise specified. It should be noted that in specifying any ranges of values, any particular upper value can be associated with any particular lower value.

For the avoidance of doubt, the word "comprising" is intended to mean "including" but not necessarily "consisting of" or "composed of". In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

Where a feature is disclosed with respect to a particular aspect of the invention (for example a composition of the invention), such disclosure is also to be considered to apply to any other aspect of the invention (for example a method of the invention) mutatis mutandis.

SUMMARY OF THE INVENTION

In a first aspect, the present invention is directed to a hair care composition comprising:
a) a copolymer;
b) an ethoxylated alkyl sulfate anionic surfactant having a formula RO(CH$_2$CH$_2$O)$_n$SO$_3$M, wherein R is an alkyl or alkenyl having from 8 to 18 carbon atoms; M is a solubilising cation comprising sodium, potassium, ammonium or mixtures thereof; the degree of ethoxylation n is 2; and
c) from 0.01 to 5% by weight of a zinc-based anti-dandruff agent;
wherein the copolymer comprises:
(i) a cationic vinyl monomer A represented by the formula (1):

$$CH_2=C(R^1)-CO-NH-(CH_2)_d N^+R^2R^3R^4 X^- \quad (1)$$

wherein $R^1$ is a hydrogen atom or a methyl group, each of $R^2$ to $R^4$ is independently a $C_{1-24}$ alkyl group, preferably a $C_{1-3}$ alkyl group, $X^-$ is independently fluoride, chloride, bromide or iodide anion, preferably chloride, and d is an integer of from 1 to 10;
(ii) a cationic vinyl monomer B represented by the formula (2):

$$CH_2=C(R^5)-CO-(O)-(CH_2)_e N^+R^6R^7R^8 Y^- \quad (2)$$

wherein $R^5$ is a hydrogen atom or a methyl group, each of $R^6$ to $R^8$ is independently a $C_{1-24}$ alkyl group, preferably a $C_{1-3}$ alkyl group, $Y^-$ is independently fluoride, chloride, bromide or iodide anion, preferably chloride, and e is an integer of from 1 to 10;
(iii) a vinyl monomer C represented by the formula (3)

$$CH_2=C(R^9)-CO-NR^{10}R^{11} \quad (3)$$

wherein $R^9$ is a hydrogen atom or methyl group, each of $R^{10}$ and $R^{11}$ is independently a hydrogen atom or a $C_{1-4}$ alkyl group, provided that the sum of carbon numbers of $R^{10}$ and $R^{11}$ is from 1 to 4; and
wherein the content of monomer A is from 1 to 44 mol % based on the total monomer content of the copolymer, the content of monomer B is from 1 to 44 mol %, and the content of monomer C is from 20 to 75 mol % based on the total monomer content of the copolymer.

In a second aspect, the present invention is directed to a packaged hair care product comprising the hair care composition of the first aspect of this invention.

In a third aspect, the present invention is directed to a method of depositing anti-dandruff agents onto scalp comprising the step of applying the hair care composition of any embodiment of the first aspect of this invention onto scalp surfaces of an individual.

All other aspects of the present invention will more readily become apparent upon considering the detailed description and examples which follow.

DETAILED DESCRIPTION

It has now been found that a hair care composition comprising a combination of a copolymer and an ethyoxylated anionic surfactant with a specific degree of ethoxylation can deliver satisfactory flocculation profile while maintaining good deposition of anti-dandruff agents.

The copolymer suitable for use in compositions of the present invention comprises constituting units of cationic vinyl monomers A and B, and constituting units of a vinyl monomer C.

The cationic vinyl monomer A is represented by the formula (1):

$$CH_2=C(R^1)-CO-NH-(CH_2)_d N^+ R^2 R^3 R^4 X^- \quad (1)$$

wherein $R^1$ is a hydrogen atom or a methyl group, each of $R^2$ to $R^4$ is independently a $C_{1-24}$ alkyl group, preferably a $C_{1-3}$ alkyl group, $X^-$ is independently fluoride, chloride, bromide or iodide anion, preferably chloride, and d is an integer of from 1 to 10;

$R^1$ is preferably a hydrogen group. Each of $R^2$ to $R^4$ which are independent of each other, is preferably a methyl group or an ethyl group, more preferably a methyl group. d is preferably an integer of from 1 to 5, more preferably 3.

The cationic vinyl monomer A of formula (1) may be a (meth)acrylamide (here "(meth)acryl" represents acryl and methacryl) having a cationic group. Illustrative yet non-limiting examples of the cationic vinyl monomer A that may be used in this invention include, for example, N-(meth)acryloylaminopropyl-N,N,N-trimethylammonium chloride, N-(meth)acryloylaminopropyl-N,N-diethyl-N-methylammonium chloride or mixtures thereof. Preferably, the cationic vinyl monomer A is N-(meth)acryloylaminopropyl-N, N,N-trimethylammonium chloride, more preferably acryloylaminopropyl-N,N,N-trimethylammonium chloride (propyltrimonium chloride acrylamide).

The cationic vinyl monomer B is represented by the formula (2):

$$CH_2=C(R^5)-CO(O)-(CH_2)_e N^+ R^6 R^7 R^8 Y^- \quad (2)$$

wherein $R^5$ is a hydrogen atom or a methyl group, each of $R^6$ to $R^8$ is independently a $C_{1-24}$ alkyl group, preferably a $C_{1-3}$ alkyl group, $Y^-$ is independently fluoride, chloride, bromide or iodide anion, preferably chloride, and e is an integer of from 1 to 10.

$R^5$ is preferably a methyl group. Each of $R^6$ to $R^8$ which are independent of each other, is preferably a methyl group or an ethyl group, more preferably a methyl group. e is preferably an integer of from 1 to 5.

The cationic vinyl monomer B of formula (2) may be a (meth)acrylic acid ester having a cationic group (here "(meth)acrylic" represents acrylic and methacrylic). Preferably, the cationic vinyl monomer B is N-(meth)acryloyloxyethyl-N,N,N-trimethylammonium chloride, more preferably N-methacryloyloxyethyl-N,N,N-trimethylammonium chloride (ethyltrimonium chloride methacrylate).

The content of monomer A is from 1 to 44 mol %, preferably from 3 to 40 mol %, more preferably from 5 to 40 mol % and most preferably from 10 to 30 mol %, based on the total monomer content of the copolymer. The content of monomer B is from 1 to 44 mol %, preferably from 3 to 40 mol %, more preferably from 5 to 40 mol %, and most preferably from 10 to 30 mol %, based on the total monomer content of the copolymer. The total content of the two cationic vinyl monomers A and B is preferably from 25 to 45 mol %, more preferably from 30 to 40 mol % based on the total monomer content of the copolymer.

The vinyl monomer C is represented by the formula (3):

$$CH_2=C(R^9)-CO-NR^{10}R^{11} \quad (3)$$

wherein $R^9$ is a hydrogen atom or methyl group, each of $R^{10}$ and $R^{11}$ is independently a hydrogen atom or a $C_{1-4}$ alkyl group, provided that the sum of carbon numbers of $R^{10}$ and $R^{11}$ is from 1 to 4.

$R^9$ is preferably a hydrogen atom. Each of $R^6$ to $R^8$ which are independent of each other, is a hydrogen atom or a $C_{1-3}$ alkyl group. The $C_{1-3}$ alkyl group may, for example, be a methyl group, an ethyl group, a propyl group or an isopropyl group. The sum of carbon numbers of $R^{10}$ and $R^{11}$ is preferably from 2 to 4, most preferably 2.

The vinyl monomer C is usually a nonionic vinyl monomer. Illustrative yet non-limiting examples of the vinyl monomer C that may be used in this invention include, for example, N-methyl(meth)acrylamide, N-ethyl(meth)acrylamide, N-propyl(meth)arylamide, N-isopropyl(meth)acrylamide, N,N-dimethyl(meth)acrylamide, N,N-diethyl(meth) acrylamide or mixtures thereof (here "(meth)acryl" represents acryl and methacryl). Preferably, the vinyl monomer C is N,N-dimethyl(meth)acrylamide, more preferably N,N-dimethylacrylamide. The vinyl monomer C may be used alone or in combination of two or more of them.

The content of vinyl monomer C is from 20 to 75 mol %, preferably from 30 to 75 mol %, more preferably from 40 to 75 mol % and most preferably from 55 to 70 mol %, based on the total monomer content of the copolymer.

However, if anionic functional groups are present in the copolymer, they may hinder formation of a complex with anionic surfactants. So in a preferred embodiment, the copolymer contains a small amount of anionic functional groups (e.g. at most 10% of the entire functional groups), and more preferably, the copolymer is substantially free of anionic functional groups. "Substantially free of", as used herein, means the copolymer shows no anionic property at pH 3 to 8.

The copolymer may further contain structural units derived from other vinyl monomers. Such other vinyl monomers may, for example, be an ester of a $C_{1-12}$ alcohol with (meth)acrylic acid; an amide of a $C_{1-22}$ alkylamine with (meth)acrylic acid; a monoester of ethylene glycol, 1,3-propylene glycol or the like with (meth)acrylic acid; an ester having a hydroxyl group or the above-mentioned monoester etherified with methanol, ethanol or the like; a nonionic monomer such as (meth)acryloyl morpholine, hydroxymethylacrylamide or hydroxyethylacrylamide; an amphoteric monomer such as a betaine group-containing (meth)acrylic ester or a betaine group-containing (meth)acrylamide; or a semi-polar monomer such as an amine oxide group-containing (meth)acrylic ester or an amine oxide group-containing (meth)acrylamide. The content of structural units derived from such other vinyl monomers in the copolymer is preferably at most 30 wt %, more preferably at most 20 wt % in the copolymer.

The content of the constituting units of the cationic vinyl monomers A and B, the vinyl monomer C, and the constituting units derived from other vinyl monomers in the copolymer may be measured by the IR absorption of the amide bond moiety; $^1$H NMR of the amide bond moiety, or the methyl group adjacent to a cationic group; or their $^{13}$C NMR.

The copolymer according to the invention preferably has a charge density of from 2.0 to 4.0 meq per gram (meq/g), more preferably from 2.1 to 3.5 meq/g, more preferably still from 2.1 to 3.0 meq/g, and most preferably from 2.5 to 3.0 meq/g. Typically, the copolymer has a molecular weight of from 10,000 gram per mole (g/mol) to 2,000,000 g/mol, more preferably from 50,000 g/mol to 1,500,000 g/mol, and most preferably from 80,000 g/mol to 1,200,000 g/mol.

The copolymer of the present invention may be produced by mixing monomers of respective constituting units or their precursors, copolymerizing them by a method such as solution polymerization, suspension polymerization or emulsion polymerization, and then carrying out a cation-forming reaction. Suitable copolymers can be prepared by known methods, such as the method disclosed in EP 1 911 778 B1. An example of such a copolymer is described as copolymer (1-7) in Table 1-1 of EP 1 911 778 B1. Another example is from Mitsubishi Chemical Corporation under the trade name Diasleek C802 or TOMICIDE C-871.

Typically, the hair care composition of the present invention comprises the copolymer in an amount of from 0.001 to 1% by weight of the hair care composition, more preferably from 0.01 to 0.5%, and most preferably from 0.03 to 0.3%, based on the total weight of the hair care composition and including all ranges subsumed therein.

The hair care composition of the present invention also comprises an ethoxylated anionic surfactant which is an ethoxylated alkyl sulfate anionic surfactant having a formula $RO(CH_2CH_2O)_nSO_3M$, wherein R is an alkyl or alkenyl group having from 8 to 18 (preferably 12 to 18) carbon atoms, M is a solubilising cation comprising sodium, potassium, ammonium, substituted ammonium or mixtures thereof, the degree of ethoxylation n is 2. An example is sodium lauryl ether sulfate (SLES).

Preferred ethoxylated alkyl sulfate anionic surfactant is sodium lauryl ether sulfate (SLES) having a degree of ethoxylation of from 0.5 to 3, preferably from 1 to 3, more preferably from 1.5 to 3, and most preferably 2.

Generally, the ethoxylated alkyl sulfate anionic surfactant in hair care composition of the present invention ranges from 0.5 to 45%, more preferably from 1 to 30%, and most preferably from 5 to 20%, based on the total weight of the hair care composition and including all ranges subsumed therein.

Typically, the hair care composition comprises the copolymer and the ethoxylated alkyl sulfate anionic surfactant in a weight ratio from 1:200 to 1:1, more preferably from 1:150 to 1:10, and most preferably from 1:100 to 1:30.

The hair care composition further comprises a zinc-based anti-dandruff agent, which are compounds that are active against dandruff and are typically anti-microbial agents and preferably anti-fungal agents. The zinc-based anti-dandruff agent is preferably water insoluble and more preferably zinc pyrithione. Zinc pyrithione (ZnPTO) shorthand for zinc 1-hydroxy-2-pyridinethione is most preferred. Preferably, zinc pyrithione is particulate having an average particle size (D50) particle size of from 0.1 to 8 microns, more preferably from 0.15 to 8 microns, more preferably still from 0.2 to 5 microns, and most preferably from 0.25 to 3 microns. Zinc pyrithione as per the above particle size is available from Kolon Life Science Inc., Sino Lion (USA) Ltd, Lonza and other suppliers.

The hair care composition of the invention comprises the zinc-based anti-dandruff agent in an amount of from 0.01 to 5%, preferably from 0.01 to 3%, more preferably from 0.05 to 2%, and most preferably from 0.05 to 1.5%, based on the total weight of the hair care composition and including all ranges subsumed therein.

Without wishing to be bound by theory, the present inventors believe that the combination of a copolymer with the specific structure and an ethoxylated anionic surfactant with the specific degree of ethoxylation provides controlled flocculation within a hair care product like shampoo, which generates smaller aggregates of anti-dandruff agents so ensures their evenly dispersity and better retention on scalp surfaces after rinsing thereby leading to higher deposition.

The pH of the composition is preferably equal to or higher than 4.0, more preferably in the range of 5.0 to 7.0.

In addition to the copolymer, the hair care composition may further comprise a minor amount of other cationic polymers. The other cationic polymer may be a homopolymer or be formed from two or more types of monomers. The molecular weight of the polymer will generally be between 5,000 and 10,000,000 g/mol, typically at least 10,000 g/mol and preferably from 100,000 to 2,000,000 g/mol. The polymers will have cationic nitrogen containing groups such as quaternary ammonium or protonated amino groups, or a mixture thereof.

The cationic nitrogen containing group will generally be present as a substituent on a fraction of the total monomer units of the cationic polymer. The ratio of the cationic to non-cationic monomer units is selected to give polymers having a DS in the required range.

Suitable further cationic polymers include, for example, copolymers of vinyl monomers having cationic amine or quaternary ammonium functionalities with water soluble spacer monomers such as (meth)acrylamide, alkyl and dialkyl (meth) acrylamides, alkyl (meth)acrylate, vinyl caprolactone and vinyl pyrrolidine. The alkyl and dialkyl substituted monomers preferably have $C_1$-$C_7$ alkyl groups, more preferably $C_{1-3}$ alkyl groups. Other suitable spacers include vinyl esters, vinyl alcohol, maleic anhydride, propylene glycol and ethylene glycol. Preferably, the further cationic polymer is cationic polysaccharide polymers, such as cationic cellulose derivatives, cationic starch derivatives and mixtures thereof.

The hair care composition may further comprise one or more cleansing surfactants in addition to the ethoxylated alkyl sulfate anionic surfactant that is included in the composition. Preferably, the cleansing surfactants are anionic surfactants.

Examples of suitable anionic cleansing surfactants are the alkyl sulphates, alkaryl sulphonates, alkanoyl isethionates, alkyl succinates, alkyl sulphosuccinates, alkyl ether sulphosuccinates, N-alkyl sarcosinates, alkyl phosphates, alkyl ether phosphates, and alkyl ether carboxylic acids and salts thereof, especially their sodium, magnesium, ammonium and mono-, di- and triethanolamine salts. The alkyl and acyl groups generally contain from 8 to 18, preferably from 10 to 16 carbon atoms and may be unsaturated. The alkyl ether sulphosuccinates, alkyl ether phosphates and alkyl ether carboxylic acids and salts thereof may contain from 1 to 20 ethylene oxide or propylene oxide units per molecule.

Typical anionic cleansing surfactants for use in hair care compositions of the invention include sodium oleyl succinate, ammonium lauryl sulphosuccinate, sodium lauryl sulphate, sodium lauryl ether sulphosuccinate, ammonium lauryl sulphate, sodium dodecylbenzene sulphonate, triethanolamine dodecylbenzene sulphonate, sodium cocoyl isethionate, sodium lauryl isethionate, lauryl ether carboxylic acid and sodium N-lauryl sarcosinate.

Suitable preferred additional anionic cleansing surfactants are sodium lauryl ether sulphosuccinate(n)EO, (where n is from 1 to 3), lauryl ether carboxylic acid (n) EO (where n is from 10 to 20).

Mixtures of any of the foregoing anionic cleansing surfactants may also be suitable.

Generally, the total amount of additional anionic cleansing surfactant in hair care composition of the present invention ranges from 0.5 to 45%, more preferably from 1.5 to 35% and most preferably from 5 to 20%, based on the total weight of the hair care composition and including all ranges subsumed therein.

In an especially preferred embodiment, the hair care composition may further comprise co-surfactants such as amphoteric and zwitterionic surfactants to provide mildness to the composition.

Examples of amphoteric or zwitterionic surfactants include alkyl amine oxides, alkyl betaines, alkyl amidopropyl betaines, alkyl sulphobetaines (sultaines), alkyl glycinates, alkyl carboxyglycinates, alkyl amphoacetates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in compositions of the invention include lauryl amine oxide, cocodimethyl sulphopropyl betaine, lauryl betaine, cocamidopropyl betaine and sodium cocoamphoacetate. Preferably, the co-surfactant is cocamidopropyl betaine (CAPB).

Typically, co-surfactant may be present in hair care compositions of the invention in an amount from 0.5 to 8% by weight of the hair care composition, preferably from 1 to 4%, based on the total weight of the hair care composition and including all ranges subsumed therein.

The hair care composition may additionally comprise a conditioning agent to provide conditioning benefit. Typically, the most popular conditioning agents used in hair care compositions are water-insoluble oily materials such as mineral oils, naturally occurring oils such as triglycerides and silicone polymers. Conditioning benefit is achieved by the oily material being deposited onto the hair resulting in the formation of a film, which makes the hair easier to comb when wet and more manageable when dry. Preferably, the conditioning agent is non-volatile, meaning that it has a vapour pressure of less than 1000 Pa at 25° C.

Preferably, the hair care composition comprises discrete dispersed droplets of a water-insoluble conditioning agent, which has a mean droplet diameter ($D_{3,2}$) of less than 15 microns, preferably less than 10 microns, more preferably less than 5 microns, most preferably less than 3 microns. The mean droplet diameter ($D_{3,2}$) of a water-insoluble conditioning agent may be measured by means of a laser light scattering technique, for example using a 2600D Particle Sizer from Malvern Instruments.

The water-insoluble conditioning agent may include non-silicone conditioning agent comprising non-silicone oily or fatty materials such as hydrocarbon oils, fatty esters and mixtures thereof. Preferably, the water-insoluble conditioning agent is emulsified silicone oil.

Suitable silicones include polydiorganosiloxanes, in particular polydimethylsiloxanes which have the CTFA designation dimethicone. Also suitable for use in compositions of this invention (particularly shampoos and conditioners) are polydimethyl siloxanes having hydroxyl end groups, which have the CTFA designation dimethiconol. Also suitable for use in compositions of this invention are silicone gums having a slight degree of cross-linking, as are described for example in WO 96/31188. Preferably, the silicone oil comprises dimethicone, dimethiconol or a mixture thereof.

The viscosity of the emulsified silicone itself (not the emulsion or the final hair care composition) is typically at least 10,000 cSt (centi-Stokes=mm$^2 \cdot$S$^{-1}$) at 25° C., preferably at least 60,000 cSt, most preferably at least 500,000 cSt, ideally at least 1,000,000 cSt. Preferably the viscosity does not exceed 10$^9$ cSt for ease of formulation. Suitable methods for measuring the kinematic viscosity of silicone oils are known to those skilled in the art, e.g. capillary viscometers. For high viscosity silicones, a constant stress rheometer can be used to measure viscosity.

Suitable emulsified silicones for use in the hair care compositions of this invention are available as pre-formed silicone emulsions from suppliers of silicones such as Dow Corning and GE silicones. The use of such pre-formed silicone emulsion is preferred for ease of processing and control of silicone particle size. Such pre-formed silicone emulsions will typically additionally comprise a suitable emulsifier, and may be prepared by a chemical emulsification process such as emulsion polymerisation, or by mechanical emulsification using a high shear mixer.

Examples of suitable pre-formed silicone emulsions include DC1785, DC1788, DC7128, all available from Dow Corning. These are emulsions of dimethiconol/dimethicone.

Another class of silicones which may be used are functionalized silicones such as amino functional silicones, meaning a silicone containing at least one primary, secondary or tertiary amine group, or a quaternary ammonium group. Examples of suitable amino functional silicones include polysiloxanes having the CTFA designation "amodimethicone."

Preferably, silicone emulsion droplets are blended with certain types of surface active block polymers of a high molecular weight to form silicone emulsions, as described for example in WO03/094874. One preferred form of the surface active block polymer having polyoxypropylene and polyoxyethylene groups as the hydrophobic and hydrophilic part respectively has formula I and has the CTFA designation poloxamer, known commercially under the trade name "Pluronic" from BASF.

I) $HO(CH_2CH_2O)_x(CH(CH_3)CH_2O)_y(CH_2CH_2O)_xH$

Suitably, the mean value of x in formula I is 4 or more, preferably 8 or more, more preferably 25 or more, yet more preferably 50 or more and most preferably 80 or more. The mean value of x is typically no greater than 200. Suitably, the mean value of y is 25 or more, preferably 35 or more, more preferably 45 or more and most preferably 60 or more. The mean value of y is typically no greater than 100.

Another preferred form of the surface active block polymer is according to formula II and has the CTFA designation Poloxamine. Those are commercially available under the trade name "Tetronic" from BASF.

II) $(HO(CH_2CH_2O)_a(CH(CH_3)CH_2O)_b)_2$—N—$CH_2$—$CH_2$—N—$((OCH_2CH(CH_3))_b(OCH_2CH_2)_aOH)_2$

Suitably, the mean value of a is 2 or more, preferably 4 or more, more preferably 8 or more, even more preferably 25 or more and most preferably 40 or more. The mean value of a is typically no greater than 200. The mean value of b is suitably 6 or more, preferably 9 or more, more preferably 11 or more and most preferably 15 or more. The mean value of b is typically no greater than 50.

Preferably, the surface active block polymer is poloxamer and/or poloxamine, more preferably, the surface active block polymer is poloxamer.

Preferably, the surface active block polymer is blended with dimethicone. The weight ratio of dimethicone to surface active block polymer in the blend is preferably in the range from 2:1 to 200:1, more preferably from 5:1 to 50:1, even more preferably from 10:1 to 40:1, most preferably from 15:1 to 30:1.

The water-insoluble conditioning agent is generally present in hair care composition of this invention in an amount from 0.05 to 15%, preferably from 0.1 to 10%, more preferably from 0.5 to 8%, most preferably from 1 to 5%, based on the total weight of the hair care composition and including all ranges subsumed therein.

Preferably the composition of the invention further comprises a suspending agent. Suitable suspending agents are selected from polyacrylic acids, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearate, alkanolamides of fatty acids having from 16 to 22 carbon atoms and mixtures thereof. Ethylene glycol distearate and polyethylene glycol 3 distearate are preferred long chain acyl derivatives, since these impart pearlescence to the composition. Polyacrylic acid is available commercially as Carbopol 420, Carbopol 488 or Carbopol 493. Polymers of acrylic acid cross-linked with a polyfunctional agent may also be used; they are available commercially as Carbopol 910, Carbopol 934, Carbopol 941 and Carbopol 980. An example of a suitable copolymer of a carboxylic acid containing monomer and acrylic acid esters is Carbopol 1342. All Carbopol (trademark) materials are available from Goodrich.

Suitable cross-linked polymers of acrylic acid and acrylate esters are Pemulen TR1 or Pemulen TR2. A suitable heteropolysaccharide gum is xanthan gum, for example that available as Kelzan mu.

Mixtures of any of the above suspending agents may be used. Preferred is a mixture of cross-linked polymer of acrylic acid and crystalline long chain acyl derivative.

The suspending agent is generally present in hair care composition of this invention in an amount of from 0.1 to 10%, more preferably from 0.5 to 6%, and most preferably from 0.5 to 4%, based on the total weight of the hair care composition and including all ranges subsumed therein.

The hair care composition of the present invention may contain other ingredients which are common in the art to enhance physical properties and performances. Suitable ingredients include but are not limited to fragrance, dyes and pigments, pH adjusting agents, pearlescers or opacifiers, viscosity modifiers, thickeners, preservatives, and natural hair nutrients such as botanicals, fruit extracts, sugar derivatives and amino acids.

The compositions of the invention are primarily intended for topical application to scalp and/or at least a portion of the hair of an individual, either in rinse-off or leave-on compositions, preferably in rinse-off compositions like shampoos.

The following examples are provided to facilitate an understanding of the present invention. The examples are not provided to limit the scope of the claims.

EXAMPLES

Example 1

This example demonstrated the flocculation profile of shampoo compositions. Compositions were prepared according to formulations detailed in Table 1. All ingredients are expressed by weight percent of the total formulation, and as level of active ingredient.

TABLE 1

| Ingredient | Samples 1 | Samples 2 |
|---|---|---|
| Sodium laureth sulphate (2EO) | 14 | 14 |
| Carbopol 980 | 0.5 | 0.5 |
| Sodium hydroxide | 0.36 | 0.36 |
| Copolymer[a] | 0.2 | — |
| Guar hydroxypropyltrimonium chloride[b] | — | 0.2 |
| Zinc sulphate heptahydrate | 0.1 | 0.1 |
| Zinc pyrithione | 0.96 | 0.96 |
| Dimethicone (DC7128)[c] | 0.8 | 0.8 |
| Dimethiconol (DC1788)[d] | 1.2 | 1.2 |
| Phenoxyethanol | 0.5 | 0.5 |
| Sodium salicylate | 0.3 | 0.3 |
| Coco amidopropyl betaine | 1.6 | 1.6 |
| Perfume | 0.75 | 0.75 |
| Sodium chloride | 1.4 | 1.4 |
| Water | Balance | Balance |

[a]Commercial copolymer has a charge density of 2.3 meq/g under the trade name Diasleek C802 from Mitsubishi Chemical Corporation.
[b]Commercial guar hydroxypropyltrimonium chloride has a charge density of from 0.67 meq/g to 0.86 meq/g and a MW of from 1,000,000 to 1,500,000 g/mol under the trade name BF13 from Ashland.
[c]Commercial dimethicone pre-blended with poloxamer from Dow corning which has a particle size of 10 μm.
[d]Commercial dimethiconol from Dow corning which has a particle size of 0.2 μm.

Methods 1 g of test shampoo sample was diluted with 9 g of water in a centrifuge tube. The tube was then vibrated on a vortex mixer for 30 seconds. Three repeats were prepared for each shampoo sample simultaneously.

The dilution was imaged immediately under the microscope. 20 μg of diluted sample was dosed onto a glass microscope slide and a coverslip placed on top. An Olympus BX51 microscope was used at 10× magnification. Three images were taken in different areas for each repeat.

The fresh made dilution was added into sample cell and the flocculation particle size distribution was measured by Malvern Master.

Results

Figure 1:
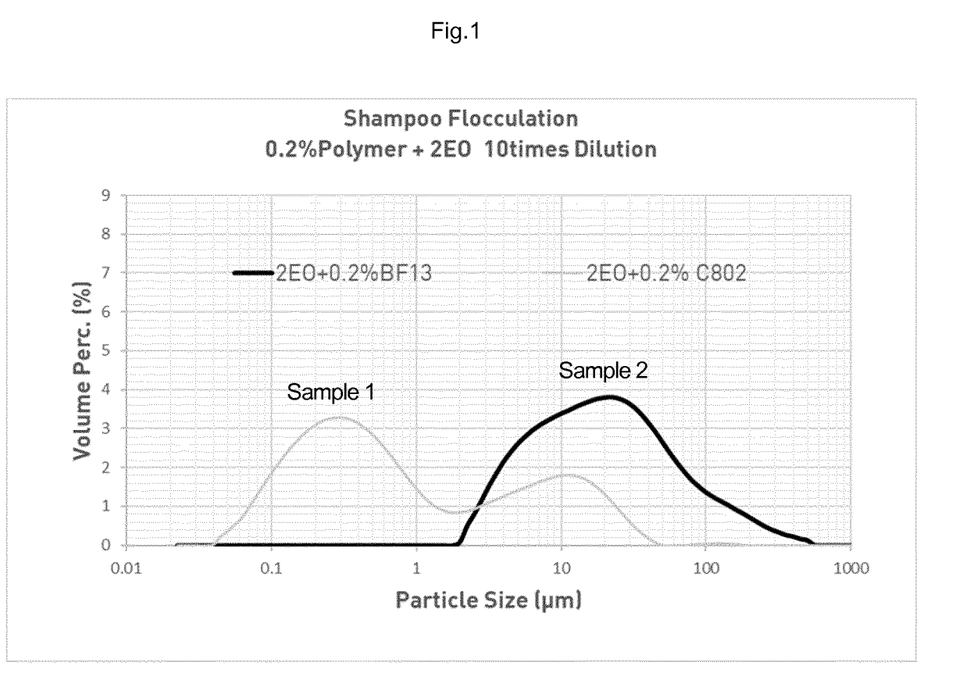
FIG. 1 shows the flocculation particle size distribution graph for samples comprising different cationic polymers.

It can be seen from the flocculation particle size distribution graph (FIG. 1) that Sample 1 comprising copolymer showed much smaller flocculation size than Sample 2 comprising guar polymers. The flocculation particle sizes of Sample 1 were located within the range of from 0.1 to 1 μm.

Microscopy images also showed that Sample 1 formed smaller flocculation size than Sample 2.

Example 2

This example demonstrated the effect of degree of ethoxylation of the anionic surfactant on the flocculation profile of shampoo compositions. All ingredients are expressed by weight percent of the total formulation, and as level of active ingredient.

TABLE 2

| Ingredient | Samples | |
| --- | --- | --- |
| | 3 | 4 |
| Sodium laureth sulphate (2EO) | 14 | — |
| Sodium laureth sulphate (3EO) | — | 14 |
| Carbopol 980 | 0.5 | 0.5 |
| Sodium hydroxide | 0.36 | 0.36 |
| Copolymer$^e$ | 0.2 | 0.2 |
| Zinc sulphate heptahydrate | 0.1 | 0.1 |
| Zinc pyrithione | 0.96 | 0.96 |
| Dimethicone (DC7128)$^c$ | 0.8 | 0.8 |
| Dimethiconol (DC1788)$^d$ | 1.2 | 1.2 |
| Phenoxyethanol | 0.5 | 0.5 |
| Sodium salicylate | 0.3 | 0.3 |
| Coco amidopropyl betaine | 1.6 | 1.6 |
| Perfume | 0.75 | 0.75 |
| Sodium chloride | 1.4 | 1.4 |
| Water | Balance | Balance |

$^e$Commercial copolymer has a charge density of 2.63 to 2.73 meq/g under the trade name TOMICIDE C-871 from Mitsubishi Chemical Corporation.

Methods

The same protocol was used to evaluate the flocculation particle size as described in Example 1.

Results

Figure 2:
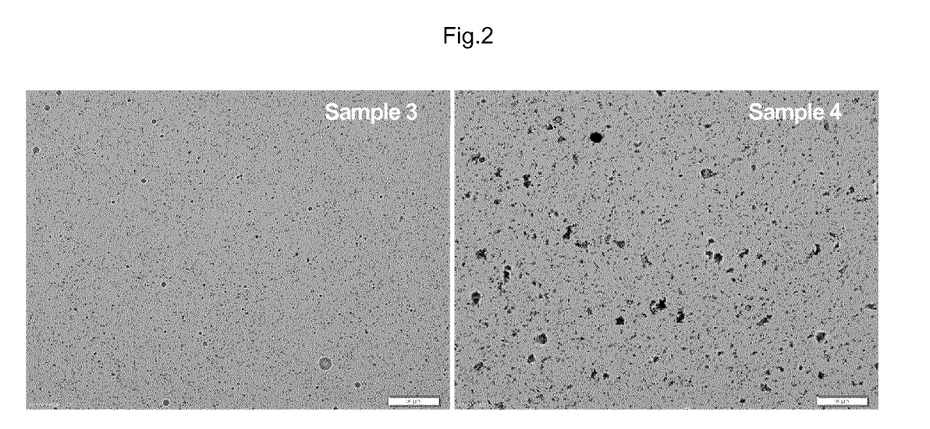
FIG. 2 shows the microscopy images for samples comprising anionic surfactants with different degree of ethoxylation at 10× magnification.
Figure 3:
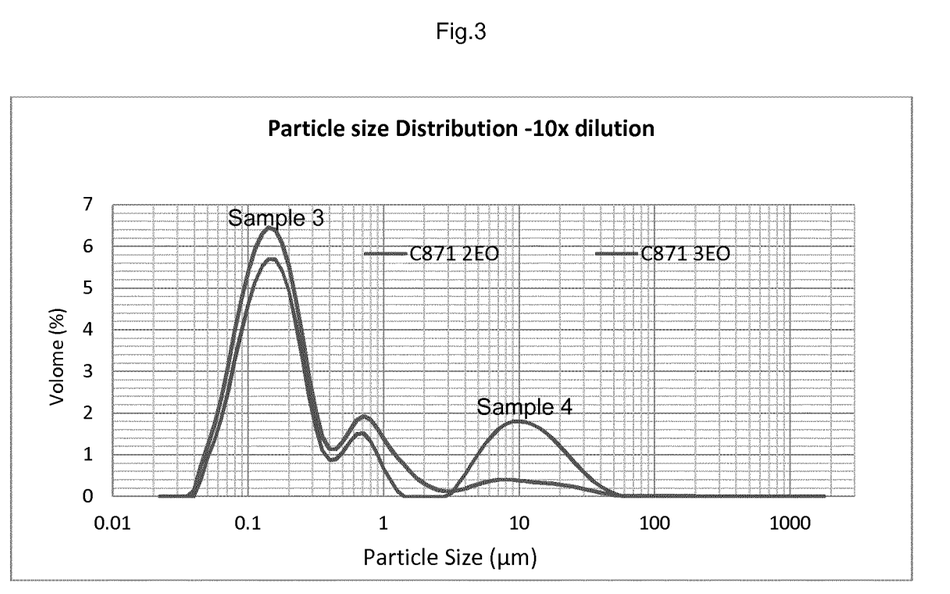
FIG. 3 shows the flocculation particle size distribution graph for samples comprising anionic surfactants with different degree of ethoxylation.

It can be seen from both microscopy images (FIG. 2) and flocculation size distribution graph (FIG. 3) that Sample 3 comprising SLES (2EO) formed smaller flocculation size than Sample 4 comprising SLES (3EO).

The invention claimed is:

1. A hair care composition comprising:
    a) from 0.01 to 0.5% by weight of a copolymer;
    b) from 5 to 20% by weight of sodium lauryl ether sulfate having a degree of ethoxylation of 2; and
    c) from 0.05 to 1.5% by weight of zinc pyrithione;
  wherein the copolymer comprises:
    (i) a cationic vinyl monomer A:
      wherein the cationic vinyl monomer A is acryloylaminopropyl-N,N,N-trimethylammonium chloride;
    (ii) a cationic vinyl monomer B:
      wherein the cationic vinyl monomer B is N-methacryloyloxyethyl-N,N,N-trimethylammonium chloride;
    (iii) a vinyl monomer C
      wherein the vinyl monomer C is N,N-dimethylacrylamide; and
    wherein the content of cationic vinyl monomer A is from 1 to 44 mol % based on the total monomer content of the copolymer, the content of cationic vinyl monomer B is from 1 to 44 mol %, and the content of vinyl monomer C is from 20 to 75 mol % based on the total monomer content of the copolymer.

2. The hair care composition as claimed in claim 1, wherein the composition comprises the copolymer and the ethoxylated alkyl sulfate anionic surfactant in a weight ratio from 1:200 to 1:1.

3. A method of depositing anti-dandruff agents onto scalp comprising the step of applying a composition as claimed in claim 1 onto scalp surfaces of an individual followed by rinsing the surfaces with water.

4. The hair composition as claimed in claim 2, wherein the composition comprises the copolymer and the ethoxylated alkyl sulfate anionic surfactant in a weight ratio from 1:150 to 1:10.

* * * * *